US007816508B2

(12) United States Patent
Leyrer

(10) Patent No.: US 7,816,508 B2
(45) Date of Patent: Oct. 19, 2010

(54) PROMOTERS FOR EXPRESSION IN MODIFIED VACCINIA VIRUS ANKARA

(75) Inventor: Sonja Leyrer, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 302 days.

(21) Appl. No.: 10/580,206

(22) PCT Filed: Oct. 27, 2004

(86) PCT No.: PCT/EP2004/012125

§ 371 (c)(1), (2), (4) Date: May 23, 2006

(87) PCT Pub. No.: WO2005/054484

PCT Pub. Date: Jun. 16, 2005

(65) Prior Publication Data

US 2008/0112971 A1 May 15, 2008

(30) Foreign Application Priority Data

Nov. 24, 2003 (DK) .............................. 2003 01730
Jan. 17, 2004 (EP) .................................. 04000943

(51) Int. Cl.
*C07H 21/04* (2006.01)
*C12N 15/00* (2006.01)
*C12N 15/63* (2006.01)

(52) U.S. Cl. .................. 536/24.1; 435/69.1; 435/320.1; 536/23.1

(58) Field of Classification Search ....................... None
See application file for complete search history.

(56) References Cited

U.S. PATENT DOCUMENTS 6,440,422 B1 8/2002 Sutter et al.
6,682,743 B2 1/2004 Mayr

FOREIGN PATENT DOCUMENTS

WO WO-02/42480 A2 5/2002
WO WO-03/097844 A1 11/2003
WO WO-2004/015118 A1 2/2004

OTHER PUBLICATIONS

Accession No. U94848.*
Antoine et al. The Complete Genomic Sequence of the Modified Vaccinia Ankara Strain: Comparison with Other Orthopoxviruses. Virology 244: 365-396, 1998.*
Shida et al.; Inprovement in 5' Upstream of A-1 Type Inclusion Body Gene of Pox Virus and Improvement in Extraneous Gene Manifestation Vector by 3' -Downstream Region of Said Gene, Derwent Abstract of JP 1202288, Aug. 15, 1989.
Mars et al.; "Characterization of Vaccinia Virus Early Promoters and Evaluation of Their Informational Content"; Journal of Molecular Biology, vol. 198, No. 4, pp. 619-631, (1987).
Chakrabarti et al.; Compact, Synthetic, Vaccinia Virus Early/Late Promoter for Protein Expression, Biotechniques, vol. 23, No. 6, pp. 1094-1097, (1997).
Davison and Moss. Structure of Vaccinia Virus Late Promoters. J. Mol. Biol, 210:771-784 (1989).

* cited by examiner

*Primary Examiner*—Michele K Joike
(74) *Attorney, Agent, or Firm*—Law Office of Salvatore Arrigo

(57) ABSTRACT

The invention concerns promoters, in particular for the expression of genes and/or coding sequences in vaccinia viruses such as Modified vaccinia virus Ankara (MVA). The invention further concerns expression cassettes comprising said promoter, vectors comprising said expression cassettes as well as pharmaceutical compositions and vaccines.

52 Claims, 1 Drawing Sheet

SEQUENCE LISTING

<160> NUMBER OF SEQ ID NOS: 12

<210> SEQ ID NO 1
<211> LENGTH: 171
<212> TYPE: DNA
<213> ORGANISM: Modified Vaccinia Virus Ankara

<400> SEQUENCE: 1
tctgcaatat tgttatcgta attggaaaaa tagtgttcga gtgagttgga ttatgtgagt 60
attggattgt atattttatt ttatatttta tattttgtag taagaataga atgctaatgt 120
caagtttatt ccaatagatg tcttattaaa aaacatatat aataaataac a 171

<210> SEQ ID NO 2
<211> LENGTH: 105
<212> TYPE: DNA
<213> ORGANISM: Modified Vaccinia Virus Ankara

<400> SEQUENCE: 2
gataaaaatt taaagtgtaa atataactat tattttatag ttgtaataaa aagggaaatt 60
tgattgtata ctttcggttc tttaaaagaa actgacttga taaaa 105

<210> SEQ ID NO 3
<211> LENGTH: 136
<212> TYPE: DNA
<213> ORGANISM: Modified Vaccinia Virus Ankara

<400> SEQUENCE: 3
gcatttcatc tttctccaat actaattcaa attgttaaat aaataatgga tagtataaat 60
agttattagt gataaaatag taaaaataat tattagaata agagtgtagt atcatagata 120
actctcttct ataaaa 136

<210> SEQ ID NO 4
<211> LENGTH: 98
<212> TYPE: DNA
<213> ORGANISM: Modified Vaccinia Virus Ankara

<400> SEQUENCE: 4
gatctataaa ggtagaccta atcgtctcgg atgaccatat atttattttc agttttatta 60
tacgcataaa tagtaaaaaa tatgttaggt ttacaaaa 98

<210> SEQ ID NO 5
<211> LENGTH: 160
<212> TYPE: DNA
<213> ORGANISM: Modified Vaccinia Virus Ankara

<400> SEQUENCE: 5
ggtaaacttt aagacatgtg tgttatacta agatggttgg cttattccat agtagcttgt 60

-continued ggaatttata aacttatgat agtaaaacta gtacccaata tgtaaagatg aaaaagtaaa 120
ttactattaa cgccgtcggt attcgttcat ccattcagtt 160

<210> SEQ ID NO 6
<211> LENGTH: 156
<212> TYPE: DNA
<213> ORGANISM: Modified Vaccinia Virus Ankara

<400> SEQUENCE: 6
atttctcggt agcacatcaa atgatgttac cacttttctt agcatgctta acttgactaa 60
atattcataa ctaattttta ttaatgatac aaaaacgaaa taaaactgca tattatacac 120
tggttaacgc ccttataggc tctaaccatt ttcaag 156

<210> SEQ ID NO 7
<211> LENGTH: 31
<212> TYPE: DNA
<213> ORGANISM: Modified Vaccinia Virus Ankara

<400> SEQUENCE: 7
tcttattaaa aaacatatat aataaataac a 31

<210> SEQ ID NO 8
<211> LENGTH: 30
<212> TYPE: DNA
<213> ORGANISM: Modified Vaccinia Virus Ankara

<400> SEQUENCE: 8
gataaaaatt taaagtgtaa atataactat 30

<210> SEQ ID NO 9
<211> LENGTH: 37
<212> TYPE: DNA
<213> ORGANISM: Modified Vaccinia Virus Ankara

<400> SEQUENCE: 9
agagtgtagt atcatagata actctcttct ataaaat 37

<210> SEQ ID NO 10
<211> LENGTH: 30
<212> TYPE: DNA
<213> ORGANISM: Modified Vaccinia Virus Ankara

<400> SEQUENCE: 10
attgttaaat aaataatgga tagtataaat 30

<210> SEQ ID NO 11
<211> LENGTH: 27
<212> TYPE: DNA
<213> ORGANISM: Modified Vaccinia Virus Ankara

<400> SEQUENCE: 11
agtaaaaaat atgttaggtt tacaaaa 27

<210> SEQ ID NO 12
<211> LENGTH: 31
<212> TYPE: DNA
<213> ORGANISM: Modified Vaccinia Virus Ankara

<400> SEQUENCE: 12
atttattttc agttttatta tacgcataaa t 31

PROMOTERS FOR EXPRESSION IN MODIFIED VACCINIA VIRUS ANKARA

Figure 1:
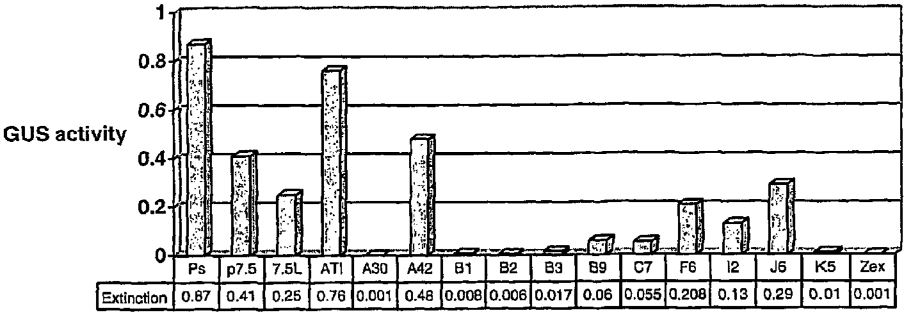

This is a U.S. National Stage of Application PCT/EP2004/012125, filed Oct. 27, 2004, which is incorporated herein by reference.

The invention concerns promoters, in particular for the expression of genes and/or coding sequences in vaccinia viruses such as Modified vaccinia virus Ankara (MVA). The invention further concerns expression cassettes comprising said promoter, vectors comprising said expression cassettes as well as pharmaceutical compositions and vaccines.

BACKGROUND OF THE INVENTION

Recombinant poxviruses are widely used to express foreign antigens in infected cells. Moreover, recombinant poxviruses are currently tested as very promising vaccines to induce an immune response against the foreign antigen expressed from the poxvirus vector. Most popular are avipoxviruses on the one side and vaccinia viruses, in particular Modified vaccinia virus Ankara (MVA) on the other side. MVA is related to vaccinia virus, a member of the genera Orthopoxvirus in the family of Poxviridae. MVA has been generated by 516 serial passages on chicken embryo fibroblasts of the Ankara strain of vaccinia virus (CVA) (for review see Mayr, A., et al. Infection 3, 6-14 [1975]). As a consequence of these long-term passages the resulting MVA virus deleted about 31 kilobases of its genomic sequence and, therefore, was described as highly host cell restricted to avian cells (Meyer, H. et al., J. Gen. Virol. 72, 1031-1038 [1991]). It was shown, in a variety of animal models that the resulting MVA was significantly aviruient (Mayr, A. & Danner, K. [1978] Dev. Biol. Stand. 41: 225-34). Additionally, this MVA strain has been tested in clinical trials as vaccine to immunize against the human smallpox disease (Mayr et al., Zbl. Bakt. Hyg. I, Abt. Org. B 167, 375-390 [1987], Stickl et al., Dtsch. med. Wschr. 99, 2386-2392 [1974]).

U.S. Pat. Nos. 5,736,368 and 6,051,410 disclose recombinant vaccinia virus strain Wyeth that expresses HIV antigens and proteins. U.S. Pat. No. 5,747,324 discloses a recombinant vaccinia virus strain NYCBH expressing lentivirus genes. EP 0 243 029 discloses a recombinant vaccinia virus strain Western Reserve expressing human retrovirus genes. WO 02/42480 discloses particularly safe and attenuated MVA strains. Recombinant MVA are disclosed inter alia in WO 98/13500 and WO 03/048184.

For the expression of heterologous genes in pox viruses only a few promoters are known to the person skilled in the art, such as the 30K and 40K promoters (see e.g. U.S. Pat. No. 5,747,324), a strong synthetic early/late promoter (see e.g. Sutter et al., Vaccine (1994) 12, 1032-40), the P7.5 promoter (see e.g. Endo et al., J. Gen. Virol. (1991) 72, 699-703) and the promoter derived from the cowpox virus A-type inclusion (ATI) gene (Li et al., J. Gen. Virol. (1998) 79, 613). All of these promoters have been used in recombinant vaccinia viruses to express heterologous genes and were shown to express said genes resulting in the production of the protein encoded by the heterologous gene. Since only a few promoters are available for the expression of genes in vaccinia virus expression systems there is general need for alternative promoters in vaccinia viruses. In addition, all of the promoters known so far are rather strong late promoters, i.e. useful for the expression of genes after the replication of the vaccinia virus vector has occurred. For some application it is desirable to have promoters allowing the expression of genes immediately after the infection of the cells, i.e. there is a need for vaccinia virus early promoters.

Moreover, as pointed out above, MVA is a very promising virus for the expression of heterologous genes due to its improved safety profile. However, all promoters known so far for the expression of heterologous genes in MVA were derived from other vaccinia viruses or are synthetic promoters for the expression in other vaccinia virus. Thus, there is also a need for promoters optimized for the expression in MVA.

DETAILED DESCRIPTION OF THE INVENTION

The invention concerns promoters derived from the genome of Modified vaccinia virus Ankara (MVA). MVA promoters were not yet known in the art.

In particular the invention concerns a promoter comprising or consisting of a nucleotide sequence selected from the group comprising:

(i) the nucleotide sequence of anyone of the following SEQ ID NO: 1 to 6:

```
                                            (SEQ ID NO: 1)
5'TCTGCAATATTGTTATCGTAATTGGAAAAATAGTGTTCGAGTGAGTTG
GATTATGTGAGTATTGGATTGTATATTTTATTTTATATTTTATATTTTGT
AGTAAGAATAGAATGCTAATGTCAAGTTTATTGCAATAGATGTCTTATTA
AAAAACATATATAATAAATAACA 3'

                                            (SEQ ID NO: 2)
5'GATAAAAATTTAAAGTGTAAATATAACTATTATTTTATAGTTGTAATA
AAAAGGGAAATTTGATTGTATACTTTCGGTTCTTTAAAAGAAACTGACTT
GATAAAA 3'

                                            (SEQ ID NO: 3)
5'GCATTTCATCTTTCTCCAATACTAATTCAAATTGTTAAATAAATAATG
GATAGTATAAATAGTTATTAGTGATAAAATAGTAAAAATAATTATTAGAA
TAAGAGTGTAGTATCATAGATAACTCTCTTCTATAAAA 3'

                                            (SEQ ID NO: 4)
5'GATCTATAAAGGTAGACCTAATCGTCTCGGATGACCATATATTTATTT
TCAGTTTTATTATACGCATAAATAGTAAAAAATATGTTAGGTTTACAAAA
3'

                                            (SEQ ID NO: 5)
5'GGTAAACTTTAAGACATGTGTGTTATACTAAGATGGTTGGCTTATTCC
ATAGTAGCTTGTGGAATTTATAAACTTATGATAGTAAAACTAGTACCCAA
TATGTAAAGATGAAAAAGTAAATTACTATTAACGCCGTCGGTATTCGTTC
ATCCATTCAGTT 3'

                                            (SEQ ID NO: 6)
5'ATTTCTCGGTAGCACATCAAATGATGTTACCACTTTTCTTAGCATGCT
TAACTTGACTAAATATTCATAACTAATTTTTATTAATGATACAAAAACGA
AATAAAACTGCATATTATACACTGGTTAACGCCCTTATAGGCTCTAACCA
TTTTCAAG 3'
```

(ii) subsequences of the sequence according to anyone of SEQ ID: No. 1 to 6

(iii) sequences having one or more nucleotide substitutions, deletions and/or insertions with respect to the sequences as defined in (i) or (ii).

SEQ ID NO: 1 to 6 are naturally part of the MVA genome and are located upstream of the reading frames A42R, J6R, F6R, I2R, C7L and B9R, respectively.

The promoters according to the present invention are preferably active as vaccinia virus promoters or active as promoters in vaccinia virus infected cells. The vaccinia virus is preferably MVA, in particular one of the MVA strains as specified below. "Active as vaccinia virus promoter" means that the promoter is able to direct the expression of a gene to which it is operably linked in a vaccinia virus after infection of cells with said virus. The cells are preferably cells that allow late and/or early expression of the vaccinia virus. "A promoter active in vaccinia virus infected cells" includes also the situation in which the promoter is not part of a vaccinia virus genome, e.g. part of a plasmid or a non-vaccinia virus viral genome; in such a situation the promoter according to the present invention is active if the cell comprising the promoter also comprises a vaccinia virus genome, e.g. if the cell is infected with a vaccinia virus. Under these circumstances the viral RNA polymerase recognizes the promoter according to the present invention and the expression of the gene/coding sequence that is linked to the promoter is activated.

According to the present invention it is possible to use anyone of the promoters as specified in SEQ ID NO: 1 to SEQ ID NO: 6. The promoter that is actually used to direct the expression of the gene/coding sequence may consist of anyone of SEQ ID NO: 1 to SEQ ID NO: 6 or the actually used promoter may be a larger structure that comprises anyone of SEQ ID NO: 1 to SEQ ID NO: 6. Alternatively it is within the scope of the present invention to use a derivative of these promoters, which may be a subsequence of the sequences as defined in anyone of SEQ. ID NO: 1 to 6. The term "subsequence of the sequences according to anyone of SEQ ID NO: 1 to 6" refers to shorter fragments of anyone of SEQ ID NO: 1 to 6 that are still active as a promoter, in particular as promoter in vaccinia virus or in vaccinia virus infected cells. Again, the vaccinia virus is preferably MVA, such as one of the strains specified below. A typical subsequence of anyone of SEQ ID NO:1 to SEQ ID NO: 6 has a length of at least 15 nucleotides, more preferably of at least 20 nucleotides, even more preferably of at least 25 nucleotides, most preferably of at least 30 nucleotides of anyone of the sequences of SEQ ID NO:1 to SEQ ID NO: 6.

A preferred subsequence of SEQ ID NO:1 is SEQ ID NO:7. A preferred subsequence of SEQ ID NO: 2 is SEQ ID NO: 8. Preferred subsequences and/or derivatives of said subsequences of SEQ ID NO: 3 are SEQ ID NO: 9 and SEQ ID NO: 10. Preferred subsequences of SEQ ID NO: 4 are SEQ ID NO: 11 and SEQ ID NO: 12. The sequences of SEQ ID NO: 6 to 12 are given in the example section.

The derivative of the promoter comprising or consisting of a nucleotide sequence of anyone of SEQ ID NO: 1 to 6 or subsequences thereof, in particular the derivative of the nucleotide sequence of SEQ ID NO: 7 to SEQ ID NO: 12 can also be a sequence that has one or more nucleotide substitutions, deletions and/or insertions with respect to any one of the sequences of SEQ ID NO:1 to 6 or subsequences thereof, in particular of the nucleotide sequences of SEQ ID NO: 7 to SEQ ID NO: 12. The derivatives according to the present invention are still active as a promoter, in particular as vaccinia virus promoter in a vaccinia virus or in vaccinia virus infected cells, more preferably as MVA promoter in MVA or in MVA infected cells. A sequence having one or more nucleotide substitutions is a sequence in which one or more nucleotides of the sequence according to anyone of SEQ ID NO: 1 to 6 or subsequences thereof, such as the sequences according to anyone of SEQ ID NO: 7 to 12 are substituted by different nucleotides. A sequence having one or more nucleotide insertions is a sequence in which one or more nucleotides are inserted at one or more locations anyone of SEQ ID NO: 1 to 6 or subsequences thereof, in particular of the nucleotide sequences of SEQ ID NO: 7 to SEQ ID NO: 12. A sequence having one or more nucleotide deletions is a sequence in which one or more nucleotides of the sequence according anyone of SEQ ID NO: 1 to 6 or subsequences thereof, in particular of the nucleotide sequences of SEQ ID NO: 7 to SEQ ID NO: 12 are deleted. In the derivatives according to the present invention deletions, substitutions and insertions may be combined in one sequence.

An example of an derivative of a subsequence according to the present invention is SEQ ID NO: 10, which is a subsequence of SEQ ID NO: 3 having in addition one nucleotide exchange with respect to the corresponding nucleotide sequence in SEQ ID NO: 3.

Preferably the derivative has a homology of at least 40%, more preferably of at least 60%, even more preferably of at least 80%, most preferably of at least 90% when compared to anyone of the sequence of SEQ ID NO: 1 to SEQ ID NO: 6 or subsequences thereof, in particular of the sequences according to anyone of SEQ ID NO: 7 to SEQ ID NO: 12. According to the most preferred embodiment not more than 10 nucleotides, even more preferably not more than 5 nucleotides are substituted, deleted and/or inserted in the sequence of anyone of SEQ ID NO: 7 to SEQ ID NO: 12.

A bundle of prior art documents allows the person skilled in the art to predict which derivatives or subsequences of anyone of SEQ ID NO: 1 to 12 still have the biological activity of being active as a vaccinia virus promoter, in particular as a promoter active in MVA. In this context reference is made to Chakrarbarti et al., Biotechniques (1997) 23, 1094-1097 and Davison and Moss, J. Mol. Biol. (1989) 210, 771-784. Moreover, whether a fragment is still active as a vaccinia virus promoter, in particular as a MVA promoter can easily be evaluated by a person skilled in the art. In particular the sequence derivative can be cloned upstream of a reporter gene in a plasmid construct. Said construct may be transfected into a eukaryotic cell or cell line, such as CEF or BHK cells that has been infected with MVA. The expression of the reporter gene is determined and compared to the expression of the reporter gene controlled by the promoter according to anyone of SEQ ID NO: 1 to 6. A derivative according to the present invention is a derivative having a promoter activity in said test system of at least 10%, preferably of at least 30%, more preferably of at least 50%, even more preferably of at least 70%, most preferably of at least 90% compared to the activity of the promoter sequence of anyone of SEQ ID NO: 1 to 6. Also those derivatives of anyone of SEQ ID NO: 1 to 12 are within the scope of the present invention that have a higher promoter activity.

The promoters according to the present invention are particularly suitable for the expression of coding sequences in MVA.

The promoter according to SEQ ID NO: 1 has a very strong activity, in particular as late promoter although it can also be used as early promoter. The same considerations apply for the corresponding subsequences such as the sequence of SEQ ID NO: 7, which is, however, particularly useful as late promoter.

The promoter according to SEQ ID NO: 2 also has a rather strong activity, in particular as late promoter. It can also be used as early promoter. The same considerations apply for the corresponding subsequences, such as the sequence of SEQ ID NO: 8, which is, however, particularly useful as late promoter.

The promoter according to SEQ ID NO: 3 is particularly useful as early promoter and has the highest early promoter activity of all promoters tested. However, it can also be used as late promoters. The same considerations apply for the corresponding subsequences, such as the sequences of SEQ ID NO: 9 and 10, respectively. Of these subsequences SEQ ID NO: 9 is particularly useful as early promoter and SEQ ID NO: 10 is particularly useful as late promoter.

The promoter according to SEQ ID NO: 4 is particularly useful if it is intended to express a linked coding sequence early and late since this promoter has a rather high activity under early as well as late conditions. The same considerations apply for the corresponding subsequences, such as the sequences of SEQ ID NO: 11 and 12, respectively. Of these subsequences SEQ ID NO: 11 is particularly useful as early promoter and SEQ ID NO: 12 is particularly useful as late promoter.

The promoters according to SEQ ID NO: 5 and 6 are particularly useful if it is intended to express linked coding sequences in rather low amounts. This is sometimes desirably if the linked coding sequence encodes a toxic gene product and/or if it is intended to induce a high avidity immune response.

The term "early promoter" refers to promoters that are active in vaccinia virus or vaccinia virus infected cells, before viral DNA replication has occurred. Methods are known to the person skilled in the art how it can be checked whether a promoter is an early promoter. In particular, the promoter of interest can be inserted upstream of a reporter gene. The construct comprising the promoter and the reporter gene are introduced into cells that are infected with a vaccinia virus. In order to assess for the activity as early promoter the cells are incubated with a substance that inhibits the DNA replication such as AraC. DNA replication is a prerequisite for the late promoter activity. Thus, any promoter activity that is measured in this assay system is due to elements active as early promoter. Consequently, the term "late promoter" refers to any promoters that are active after DNA replication has taken place. The late activity can also be measured by methods known to the person skilled in the art. For the sake of simplicity the term "late promoter" as used in the present application refers to the activity of a promoter that is determined if no substance is added that blocks DNA replication.

According to a further embodiment the present invention refers to an expression cassette comprising the promoter according to the present invention and a coding sequence, wherein the expression of the coding sequence is controlled by said promoter. The expression cassette is preferably not an expression cassette that occurs naturally in the genome of a vaccinia virus. Thus, if the promoter according to the present invention is a promoter that naturally occurs in the genome of the vaccinia virus the sequence to which the promoter is linked is preferably different from the sequence to which the promoter is naturally linked in the vaccinia virus genome. In other words, if the promoter according to the present invention is identical to a naturally occurring promoter the coding sequence the expression of which is controlled by the promoter and/or the sequences located between the promoter and the coding sequence are different from the corresponding sequences to which said promoter is naturally linked. The term "different" in this context refers to sequences that show at least one nucleotide difference in said sequence. Preferably it is the coding sequence which has at least one nucleotide difference. According to other alternatives the homology between the coding sequence in the expression cassette and the sequence to which the promoter is naturally linked is less than 90%, less than 80%, less than 70%, less than 60%, less than 50%, less than 40% or even less than 20%. Most preferably the coding sequence that is controlled by the promoter according to the present invention codes for a peptide/protein having a difference of at least one amino acid compared to the naturally occurring protein encoded by said coding sequence. By way of example the expression cassette is not the expression cassette comprising the naturally occurring vaccinia virus C7L promoter directing the expression of the naturally occurring C7L gene, e.g. the expression cassette is not the expression cassette disclosed in WO2004/015118 comprising the C7L promoter and the C7L coding sequence.

On the other hand, if the sequence which should be expressed is a naturally occurring vaccinia virus sequence the promoter that is used to express said sequence is different from the promoter that is directs the expression of the coding sequence in the natural context. According to this alternative the nucleotide sequence of the promoter differs in at least one nucleotide from the sequence of the naturally occurring vacciniavirus promoter. According to other alternatives the homology between the promoter according to the present invention that controls the expression of the vaccinia virus sequence and the naturally occurring promoter linked to the vaccinia virus sequence is less than 90%, less than 80%, less than 70%, less than 60%, less than 50% or even less than 40%.

Preferably the coding sequence may code for at least one antigenic epitope or antigen, therapeutic peptides or proteins, antisense RNA or ribozymes. If the coding sequence encodes an antigenic epitope or antigen the expression cassette may be used to express said antigen after introduction of said expression cassette in cells in an organism, e.g. a mammalian animal including a human. The presentation of said antigen/epitope may elicit an immune response in the organism that may lead to a vaccination of the organism against the agent from which the antigen/epitope is derived. More specifically the epitope/antigen may be part of a larger amino acid sequence such as a polyepitope, peptide or protein. Preferably the coding sequence codes for at least one antigenic epitope or antigen, therapeutic peptides or proteins, antisense RNA or ribozymes which are not encoded by a vaccinia virus genome.

Examples for such polyepitopes, peptides or proteins may be polyepitopes, peptides or proteins derived from (i) viruses, in particular viruses other than vaccinia viruses, such as HIV, HTLV, Herpesvirus, Denguevirus, Poliovirus, measles virus, mumps virus, rubella virus, Hepatitis viruses and so on, (ii) bacteria, (iii) fungi, (iv) tumor related polypeptides/proteins such as tumor related antigens.

Alternatively the coding sequence may encode a therapeutic compound such as interleukins, interferons, ribozymes or enzymes.

In more general terms the invention concerns any nucleic acid sequence comprising the promoter according to the present invention and/or the expression cassette according to the present invention. The nucleic acid may be RNA, e.g. if the promoter is part of a retroviral genome. More preferably the nucleic acid is DNA. The DNA may be any type of DNA such as linear, circular, single stranded or double stranded DNA.

According to a further embodiment the promoter and/or expression cassette according to the present invention may be part of a vector. The term "vector" refers to any vectors known to the person skilled in the art. A vector can be a plasmid vector such as pBR322 or a vector of the pUC series. More preferably the vector is a virus vector. In the context of the present invention the term "viral vector" or "virus vector" refers to an infectious virus comprising a viral genome. In this case the DNA of the present invention is part of the viral genome of the respective viral vector. The recombinant viral genome is packaged and the obtained recombinant vectors can be used for the infection of cells and cell lines, in-particular for the infection of living animals including humans. Typical virus vectors that may be used according to the present invention are adenoviral vectors, retroviral vectors or vectors on the basis of the adeno associated virus 2 (AAV2). Most preferred are poxviral vectors. The poxvirus may be preferably a canarypox virus, a fowlpoxvirus or a vaccinia virus.

More preferred is modified vaccinia virus Ankara (MVA) (Sutter, G. et al. [1994], Vaccine 12: 1032-40; Antoine, G. et al. [1998], Virology 244: 365-396). The term "MVA" as used in the present application refers to any MVA strain known in the prior art. An example for an MVA strain is deposit VR-1508, deposited at the American Type Culture collection (ATCC), Manassas, Va. 20108, USA. Further examples for MVA virus strains used according to the present invention are strains MVA 572 and 575 deposited at the European Collection of Animal Cell Cultures (ECACC), Salisbury (UK) with the deposition number ECACC V94012707 and ECACC V00120707, respectively, MVA-BN with the deposition number ECACC V00083008.

The most preferred MVA-strain is MVA-BN or a derivative thereof. The features of MVA-BN, the description of biological assays allowing to evaluate whether a MVA strain is MVA-BN or a derivative thereof and methods allowing to obtain MVA-BN or a derivative thereof are disclosed in WO 02/42480. The content of this application is included in the present application by reference. In particular, reference is made to the definition of the properties of vaccinia virus according to the invention as described in WO 02/42480, such as the properties of MVA and the properties and definitions of the derivates of MVA-BN. Said reference also discloses how MVA and other vaccinia viruses can be propagated. Briefly, eukaryotic cells are infected with the virus. The eukaryotic cells are cells that are susceptible to infection with the respective poxvirus and allow replication and production of infectious virus. For MVA an example for this type of cells are chicken embryo fibroblasts (CEF) and BHK cells (Drexler I., Heller K., Wahren B., Erfle V. and Sutter G. "Highly attenuated modified vaccinia Ankara replicates in baby hamster kidney cells, a potential host for virus propagation, but not in various human transformed and primary cells" J. Gen. Virol. (1998), 79, 347-352). CEF cells can be cultivated under conditions known to the person skilled in the art. Preferably the CEF cells are cultivated in serum-free medium in stationary flasks or roller bottles. The incubation preferably takes place 48 to 96 hours at 37° C.±20° C. For the infection MVA is preferably used at a multiplicity of infection (MOI) of 0.05 to 1 $TCID_{50}$ and the incubation preferably takes place 48 to 72 hours at 37° C.±2° C.

Methods are known to the person skilled in the art how the expression cassette or the promoter according to the present invention can be inserted into a viral genome, in particular into the genome of a vaccinia virus, most preferably into the genome of MVA. By way of example, the expression cassette or the promoter or derivative thereof according to the present invention may be inserted into the genome of MVA by homologous recombination. To this end a nucleic acid is transfected into a permissive cell line such as CEF or BHK cells, wherein the nucleic acid comprises the expression cassette or the promoter or derivative thereof according to the present invention flanked by nucleotide stretches that are homologous to the region of the MVA genome in which the expression cassette or the promoter or derivative thereof according to the present invention is to be inserted. The cells are infected by MVA and in the infected cells homologous recombination occurs between the nucleic acid and the viral genome. Alternatively it is also possible to first infect the cells with MVA and then to transfect the nucleic acid into the infected cells. Again recombination occurs in the cells. The recombinant MVA is then selected by methods known in the prior art. The construction of recombinant MVA is not restricted to this particular method. Instead, any suitable method known to the person skilled in the art may be used to this end.

The expression cassette or the promoter according to the present invention may be introduced into any suitable part of the vector, in particular into a viral genome. In case of vaccinia viruses the insertion may be made into non-essential parts of the viral genome or into an intergenic region of the viral genome. The term "intergenic region" refers preferably to those parts of the viral genome located between two adjacent genes that do not comprise coding sequences. If the vector is MVA the insertion may also be made into a naturally occurring deletion site of the viral genome. The term "naturally occurring deletion site" refers to those parts of the viral genome that are deleted with respect to the genome of the vaccinia virus Copenhagen strain. However, the insertion sites are not restricted to these preferred insertion sites in the vaccinia virus genome and the MVA genome, since it is within the scope of the present invention that the expression cassette may be inserted anywhere in the viral genome as long as it is possible to obtain recombinants that can be amplified and propagated in at least one cell culture system, such as Chicken Embryo Fibroblasts (CEF cells).

The promoter according to the present invention may be used to express a gene that is already part of the vector, e.g. the genome of MVA. Such a gene may be a gene that is naturally part of the viral genome or a foreign gene that has already been inserted into the vector. In these cases the promoter according to the present invention is inserted upstream of the gene in the vector, the expression of which is to be controlled by the promoter. A MVA vector comprising an expression cassette according to the present invention can also be made by replacing anyone of the open reading frames A42R, J6R, F6R, I2R, C7L and B9R by a coding sequence the expression of which is to be controlled by the promoter naturally controlling the expression of anyone of said open reading frames. Thus, by way of example the A42R coding sequence or parts thereof may be replaced by the coding sequence, which is to be expressed. In the resulting construct said coding sequence is controlled by a promoter according to the present invention, namely by the promoter sequence according to SEQ ID NO: 1 and SEQ ID NO: 7. These expression cassettes are also within the scope of the present invention.

According to a further embodiment the invention concerns the vector according to the present invention as vaccine or medicament. In more general term the invention relates to a vaccine or pharmaceutical composition comprising an expression cassette, a DNA or a vector according to the present invention. Methods are known to the person skilled in the art how the vaccine or pharmaceutical composition can be administered to the animal or human body. In case of DNA and plasmid vectors the DNA and the vector can simply be administered by injection. If the vector is a viral vector such as a vaccinia virus vector, in particular a MVA vector it may also be administered to the animal or human body according to the knowledge of the person skilled in the art, e.g. by intra venous, intra muscular, intra nasal, intra dermal or subcutaneous administration. Further details on the amount of virus administered are given below.

The pharmaceutical composition or the vaccine may generally include one or more pharmaceutical acceptable and/or approved carriers, additives, antibiotics, preservatives, adjuvants, diluents and/or stabilizers in addition to the promoter, expression cassette or vector according to the present invention. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of pharmaceutical compositions or vaccines, the DNA, expression cassette or vector according to the present invention, in particular a recombinant vaccinia virus such as recombinant MVA is converted into a physiologically acceptable form. For vaccinia viruses, in particular MVA this can be done based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titre of $5\times10^8$ $TCID_{50}$/ml formulated in about 10 mM Tris, 140 mM NaCl pH 7.4. For the preparation of vaccine shots, e.g., $10^1$-$10^9$ particles of the recombinant virus according to the present invention are lyophilized in phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. A typical virus containing formulation suitable for freeze-drying comprises 10 mM Tris-buffer, 140 mM NaCl, 18.9 g/l Dextran (MW 36000-40000), 45 g/l Sucrose, 0.108 g/l L-glutamic acid mono potassium salt monohydrate pH 7.4. The glass ampoule is then sealed and can be stored between 4° C. and room temperature for several months. However, as long as no need exists the ampoule is stored preferably at temperatures below −20° C.

For vaccination or therapy the lyophilisate or the freeze-dried product can be dissolved in 0.1 to 0.5 ml of an aqueous solution, preferably water, physiological saline or Tris buffer, and administered either systemically or locally, i.e. by parenteral, intramuscular or any other path of administration know to the skilled practitioner. The mode of administration, the dose and the number of administrations can be optimized by those skilled in the art in a known manner.

Thus, according to a related embodiment the invention relates to a method for affecting, preferably inducing an immunological response in a living animal body including a human comprising administering the expression cassette, the DNA, the vector, the pharmaceutical composition or the vaccine according to the present invention to the animal or human to be treated. If the vaccine is a vaccinia virus, in particular MVA a typical vaccine shot for humans comprises at least $10^2$, preferably at least $10^4$, more preferably at least $10^6$, even more preferably $10^7$ or $10^8$ $TCID_{50}$ (tissue culture infectious dose) of the virus.

If the vaccine is a recombinant MVA, in particular recombinant MVA-BN and its derivatives that the virus may be used for prime-boost administration. Thus, the invention further relates to a method, wherein the vector is MVA, in particular MVA-BN and its derivatives, and wherein said vector or the composition or the vaccine comprising said vector is administered to an animal, including a human in need thereof, in therapeutically effective amounts in a first inoculation (“priming inoculation”) and in a second inoculation (“boosting inoculation”).

The invention further concerns a method for introducing a coding sequence into a target cell comprising the introduction of the vector, the expression cassette or of the DNA according to the present invention into the target cell. If the vector is a vaccinia virus, in particular MVA such as MVA-BN the target cell may be a cell in which the virus is able to replicate such as CEF or BHK cells or a cell that can be infected by MVA, but in which the virus does not replicate (such as all types of human cells for MVA-BN).

The invention further relates to a method for producing a peptide, protein and/or virus comprising the infection of a host cell with a virus vector according to the present invention, followed by the cultivation of the infected host cell under suitable conditions, and further followed by the isolation and/or enrichment of the peptide and/or protein and/or viruses produced by said host cell. If it is intended to produce, i.e. amplify the virus according to the present invention the cell has to be a cell in which the virus is able to replicate. For vaccinia viruses, in particular MVA suitable cells are CEF or BHK cells. If it is intended to produce a peptide/protein encoded by the virus vector according to the present invention the cell may be any cell that can be infected by the virus vector and that allows the expression of the virus encoded proteins/peptides.

The invention further relates to a method for producing a peptide, protein and/or virus comprising the transfection of a cell with the expression cassette, the DNA or the plasmid vector according to the present invention, followed by the infection of the cell with a vaccinia virus. The infected host cell is cultivated under suitable conditions. A further step comprises the isolation and/or enrichment of the peptide and/or protein and/or viruses produced by said host cell. The step of infecting the cells with a vaccinia virus may be made before or after the step of transfection of the cells.

The invention further relates to cells comprising a promoter, DNA, expression cassette or vector according to the present invention. In particular the invention relates to cells infected with the virus vector according to the present invention.

SHORT DESCRIPTION OF THE FIGURES

FIG. 1: GUS activity after expression by different promoters Cells were infected with MVA-BN and transfected with the appropriate plasmids. After 48 hours the cells were extracted and the GUS activity was determined indirectly by measuring the extinction at 415 nm after an enzymatic reaction, which causes the development of yellow colour. Zex=negative control (MVA-BN infected cells).

Figure 2:
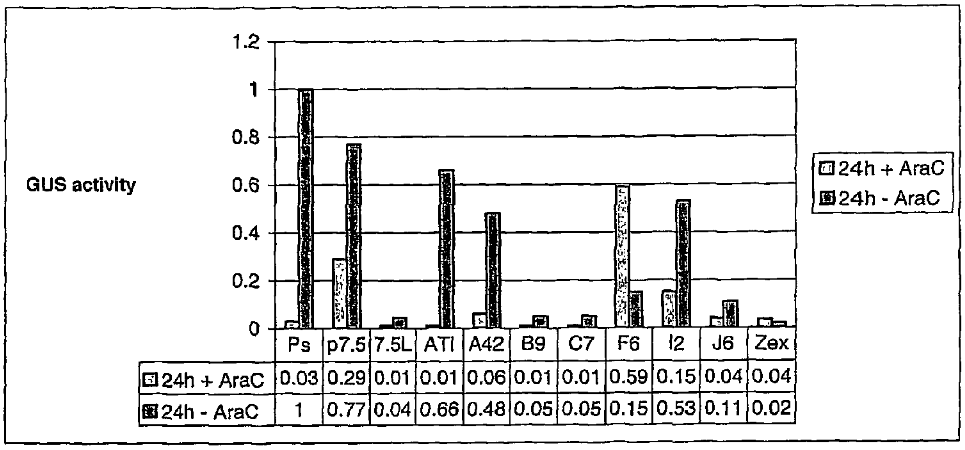

FIG. 2: GUS activity after early and early/late expression Cells were infected with MVA-BN and transfected with the appropriate plasmids. After 24 hours cells were extracted and the GUS activity was determined indirectly by measuring the extinction at 415 nm after an enzymatic reaction, which causes the development of yellow colour. Zex=negative control (MVA-BN infected cells). For that enzymatic reaction, samples without AraC (early+late) expression had to be incubated for 5 hours, the one with AraC (early expression) had to be incubated over night in order to obtain a color reaction.

Figure 3:
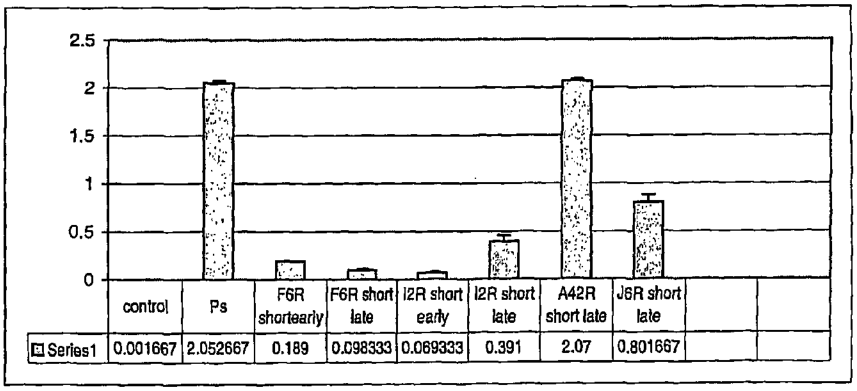

FIG. 3: GUS activity after expression by different promoters Cells were infected with MVA-BN and transfected with the appropriate plasmids. After 24 hours the cells were extracted and the GUS activity was determined indirectly by measuring the extinction at 415 nm after an enzymatic reaction, which causes the development of yellow colour. Control=negative control (MVA-BN infected cells).

EXAMPLES

The following example(s) will further illustrate the present invention. It will be well understood by a person skilled in the art that the provided example(s) in no way may be interpreted in a way that limits the applicability of the technology provided by the present invention to this example(s).

Example 1

Analysis of Promoters to Express Coding Sequences in the MVA-BN Genome 1.1 Aim of the Experiment:

It was the aim of this analysis to identify promoters that are suitable to express coding sequences in the MVA genome, preferably coding sequences that are heterologous to the natural MVA genome. Especially for the insertion of two or more genes in a single insertion site it is advantageous to use different promoters for expression of the single genes in order to reduce the risk of recombination events, which could result in deletion of one of the foreign genes. Furthermore it is desirable to have promoters of different strength in order to have the possibility to express the foreign genes inserted in recombinant MVA-BN in variable amounts, depending on the strength of the promotor. 11 putative promoters were isolated in total. These putative promoter sequences were cloned in a plasmid backbone (pBSKS+). In order to analyse their potential activity, the promoters were fused to the GUS (*E. coli* β-Glucuronidase) reporter gene. BHK (baby hamster kidney) cells were infected with MVA-BN and transfected with the plasmids containing the putative promoters fused to the GUS gene. If the promoter was functional, GUS was expressed and could be quantified by an enzymatic reaction of GUS. As positive control and as reference the well-characterized Vaccinia virus promoter's p7.5 and Ps were fused to GUS and analysed in parallel. By measurement of the GUS expression the putative promoters were screened on activity, strength and early/late expression. The early/late expression was checked by adding AraC (Arabinosid Cytosine) to the culture media. The promoters, which are shown to be functional, namely the Ps, p7.5, 7.5L and ATI promoter which were known in the prior art as well as the newly identified promoter sequences that are naturally involved in the expression control of the MVA ORF's, A42L, B9R, C7L, F6R, I2R, J6R preferably can be used for the expression of foreign genes in recombinant MVA constructs (recMVA-BN).

1.2 Material

| | |
|---|---|
| Cells: | BHK cells |
| Virus: | MVA-BN standard crude stock ($7.5 \times 10^7$ $TCID_{50}$) |
| DNA: | pAB-GUS (Ps promoter + GUS) |
| | pBNX71 (pBluescript + Vaccinia virus pr7.5 + GUS) |
| | pBNX73 (pBluescript + Cowpox virus ATI promoter + GUS) |
| | pBN81 (pBluescript + modified H5R promoter + GUS1) |
| | pBN61 (pBluescript + MVA B1R promoter + GUS) |
| | pBN62 (pBluescript + MVA B2R promoter + GUS) |
| | pBN63 (pBluescript + MVA B3R promoter + GUS) |
| | pBN6O (pBluescript + MVA A30R promoter + GUS) |
| | pBN82 (pBluescript + Vaccinia virus 7.5 L promoter + GUS) |
| | pBN83 (pBluescript + MVA C7L promoter (SEQ ID NO: 5 + GUS) |
| | pBNX49 (pBluescript + MVA A42R promoter (SEQ ID NO: 1) + GUS) |
| | pBNX69 (pBluescript + MVA I2R promoter (SEQ ID NO: 4) + GUS) |
| | pBNX72 (pBluescript + MVA K5L promoter + GUS) |
| | pBNX83 (pBluescript + MVA F6R promoter (SEQ ID NO: 3) + GUS) |
| | pBNX84 (pBluescript + MVA B9R promoter (SEQ ID NO: 6 + GUS) |
| | pBNX85 (pBluescript + MVA J6R promoter (SEQ ID NO: 2) + GUS) |
| Transfection kit: | Effectene transfection kit (Qiagen) |
| Media and Supplements: | DMEM (Gibco BRL) with 10% FCS (Gibco BRL) |
| Chemicals and Buffers: | Lysisbuffer (PBS + 0.1% Triton + 1 mM protease inhibitor) |
| AraC (Sigma, Cat. No. 01768) | |
| GUS substrate 1 mM (p-Nitrophenyl-beta-(D)-glucuronide; Sigma, Cat. No. N1627) | |
| Stop solution 2.5 M (2-amino-2-methyl-1,3-propandiol; Sigma, Cat. No. A9754) | |

1.3 Methods

Seeding of Cells $5\times10^5$ BHK cells were seeded per transfection reaction in a well of a 6-well-plate and maintained in DMEM/10% FCS over night at 37° C. and 5% $CO_2$.

Infection/transfection Cells were infected with MVA-BN (moi 0.1) in 0.5 ml DMEM/10% FCS per well and incubated for 1 h at room temperature on a shaker. Transfection was performed as described in the manufacturers protocol. 2 μg plasmid were diluted in buffer EB (100 μl total volume). After addition of 3.2 μl enhancer solution the solution was mixed and incubated for 5 min. at room temperature. Then 10 μl Effectene reagent was added, suspension was mixed and incubated for 10 min. at room temperature. The virus-suspension was removed from the cells and 1.6 ml DMEM/10% FCS were added. 0.6 ml DMEM/10% FCS were added to the DNA Effectene mixture and dropped on the cells while rotating the culture plate. Cells were then incubated 7, 24 or 48 hours dependent on the analysis. For the analysis of early/late expression AraC was added to the medium during infection and transfection (40 μg/ml).

Harvesting of the Cells

Medium was removed from cells and 0.5 ml of Lysis buffer was added. After shaking 15 min. at RT, cells were scraped in the Lysis buffer, transferred to a 1.5 ml reaction tube and vortexed vigorously. Lysed cells were centrifuged for 1 min. at 500 rcf and 4° C., the clear supernatant was transferred to a fresh vial and stored at −20° C. until use.

Determination of GUS Activity

10 μl of cell extract (=protein out of $2\times10^4$ cells) was added to 1 ml pre-warmed substrate solution (37° C.) and incubated at 37° C. until a yellow colour was developed. Samples were then placed on ice immediately and 0.4 ml stop solution was added. The Extinction at 415 nm was determined and equated with the GUS activity as extinction values between 0.05 and 2.0 are in a linear range. The substrate solution was used as reference and a cell extract of MVA-BN infected cells was used as negative control.

1.4 Experiments and Results

Experiment 1: Determination of Function of Putative Promoters

For the first experiment all plasmids, which contain a putative MVA promoter or a well-characterized promoter fused to the GUS gene, were analysed. Cells were infected with MVA-BN (moi 0.1) and transfected with the corresponding plasmid. Cells were harvested after 48 hours, lysed and GUS activity was determined. This experiment was performed in order to determine, which promoters are functional. The results are shown in FIG. 1.

The negative control (extract from MVA-BN infected cells) clearly showed no GUS activity (Zex; extinction 0.001). The well-characterized strong synthetic Ps promoter was shown to be very efficient (Ps; extinction 0.87) as there was a high amount of GUS detectable after 48 hours of expression. The also well-known naturally occurring Vaccinia virus pr7.5 promoter did show also a quite high activity (p7.5; extinction 0.41). Also the late portion of pr7.5 (7.5L; extinction 0.25) shows a clearly detectable activity. The Cowpox ATI promoter clearly showed to be very efficient for the expression of foreign genes by MVA-BN (ATI; extinction 0.76). For the putative promoter regions of the MVA-BN genome, it was shown that A42R (A42; extinction 0.48), B9R (B9; extinction 0.06), C7L (C7; extinction 0.055), F6R (F6; extinction 0.208), I2R (12; extinction 0.130) and J6R (J6; extinction 0.290) are functional promoters. The promoters, which clearly showed to be active (extinction>0.05) in the first preliminary experiment, were characterized in more detail (Experiment 2).

Experiment 2: Characterization of Expression of Promoters

The promoters, which did show activity in experiment 1 were characterized on their pattern of expression. For that purpose, the cells infected with MVA-BN and transfected with the corresponding plasmid were incubated with AraC. AraC inhibits the DNA replication, which is an essential prerequisite for the late expression of genes during the MVA replication cycle. In parallel the same experiment was performed without addition of AraC. Infected and transfected cells were harvested after 24 hours and the GUS activity was determined in triplicate. FIG. 2 shows the average extinction of each sample.

After incubation without AraC (−AraC) for 24 hours, the total GUS expression (early+late) is clearly detectable for all promoters (FIG. 2: right columns). The strength of the newly identified promoters in declining succession is: I2R (12) >A42R (A42)>F6R (F6)>J6R (J6)>B9R (B9)=C7L (C7).

The promoters B9, C7 and J6 were shown to be mainly involved in the late expression during the life cycle of MVA, as incubation with AraC (+AraC), which inhibits late expression, results in an expression-level of GUS comparable to that of the negative control (Zex). Although the C7L promoter appeared to be rather weak several hints exist, that it plays an important role during early expression.

The promoters A42R, 12R and F6R clearly show a very efficient early expression. As for the determination of the early expression the samples had to be incubated over night in order to get a detectable color reaction. These results cannot be compared to the values of the early+late expression (FIG. 2: −AraC) directly as they only were incubated for 5 hours. The promoters, which did show early expression were analysed again after 7 hours of expression and the results after 24 hours could be confirmed (data not shown).

1.5 Conclusion

It was clearly shown, that promoters of different strength could be obtained and that there is now a spectrum of different promoters available, which show different expression patterns dependent on the incubation period and on the possibility of MVA-BN to replicate. If early+late expression is preferred, promoters A42R, I2R and F6R are preferably used. If the early expression should be avoided (e.g. for foreign genes, which contain the stop signal TTTTTNT for early expression), the promoters B9R, J6R or C7L are preferably used.

Example 2

Analysis of Minimal Promoter Elements Derived from SEQ ID NO: 1 to 4

In example 1 several sequences have been identified that are particularly suitable to express foreign genes in the MVA genome. In order to check whether shorter fragments fulfill the same purpose additional experiments were carried out. Shorter fragments of SEQ ID NO 1 to 4 were isolated by PCR and cloned in a plasmid backbone (pBSKS+). In total 6 putative minimal promoters were tested. In order to analyse their potential activity, the promoters were fused to the GUS reporter gene. BHK cells were infected with MVA-BN and transfected with the plasmids containing the putative minimal promoters fused to the GUS gene. By measurement of the GUS expression the putative promoters were screened on activity and strength of expression (see example 1). As positive control and as reference the well-characterized Vaccinia virus late promoter Ps was fused to GUS and analysed in parallel. The minimal promoter elements of about 30 bp can be used for the expression of foreign genes in recombinant MVA constructs (recMVA-BN) without the risk of homologous recombination between the homolgous sequences of the original and the additionally cloned promoter.

2.1 Material and Method

If not indicated otherwise the materials and methods used in example 2 correspond to the methods in example 1. PCR was made according to standard techniques.

2.2 Experiments and Results

Fusion of promoters to GUS gene by PCR The PCR reactions resulted in the fusion of the following minimal promoter sequences to the GUS gene:

```
SEQ ID NO: 7 ("A42 short late")
TCTTATTAAAAAACATATATAATAAATAACA

SEQ ID NO: 8 ("J6R short late")
GATAAAAATTTAAAGTGTAAATATAACTAT

SEQ ID NO: 9 ("F6R short early)
AGAGTGTAGTATCATAGATAACTCTCTTCTATAAAAT

SEQ ID NO: 10 ("F6R short late")
ATTGTTAAATAAATAATGGATAGTATAAAT

SEQ ID NO: 11 ("I2R short early")
AGTAAAAAATATGTTAGGTTTACAAAA

SEQ ID NO: 12 ("I2R short late")
ATTTATTTTCAGTTTTATTATACGCATAAAT
```

All putative minimal promoters fused to the GUS gene were cloned in pBSKS+and sequenced.

Determination of Function of the Putative Minimal Promoters

In order to analyse functionality of the putative minimal promoter elements the BHK cells were infected with MVA-BN (moi 1.0) and transfected with the corresponding plasmid. Cells were harvested after 24 hours, lysed and GUS activity was determined (FIG. 3).

The negative control (extract from MVA-BN infected cells) clearly showed no GUS activity (control; average extinction 0.00167). The well-characterized strong synthetic Ps promoter was shown to be very efficient (Ps; average extinction 2.05267) as there was a high amount of GUS detectable after 24 hours of expression. For the putative promoter minimal promoter elements of the MVA-BN genome, it was shown that all of F6R short early, F6R short late, I2R short early, I2R short late, A42R short late and J6R short late are functional promoters.

In total six functional minimal promoter elements were isolated. Two are suitable for the weaker early transcription (I2R short early: average extinction 0.06933; F6R short early: average extinction 0.189) and four are suitable for late expression of different levels (F6R short late: average extinction: 0.09833; I2R short late: average extinction 0.391; J6R short late: average extinction: 0.80167 and A42R short late: average extinction 2.07).

2.3 Conclusion

It was clearly shown, that promoters of different strength could be isolated and that there is now a spectrum of different promoters available. If early expression is preferred, the minimal promoter F6R short early or I2R short early are preferably used. If the late expression is preferred and early expression should be avoided (e.g. for foreign genes, which contain the stop signal TTTTTNT for early expression), the minimal promoter elements F6R short late, I2R short late, J6R short late and A42R short late are preferably used.

The invention claimed is:

1. An isolated DNA consisting of any one of the sequences of SEQ ID NO:3, SEQ ID NO:4, SEQ ID NO:6, SEQ ID NO:8, SEQ ID NO:9, SEQ ID NO:10, SEQ ID NO:11, and SEQ ID NO:12, wherein the isolated DNA is active as a modified vaccinia virus Ankara promoter or active as a promoter in vaccinia virus infected cells.

2. An isolated DNA consisting of a derivative of any one of the sequences of SEQ ID NO:8, SEQ ID NO:9, SEQ ID NO:10, SEQ ID NO:11, and SEQ ID NO:12;

wherein no more than 10 nucleotides are substituted in the derivative relative to the sequence of SEQ ID NO:8, SEQ ID NO:9, SEQ ID NO:10, SEQ ID NO:11, or SEQ ID NO:12; and wherein the isolated DNA is active as a modified vaccinia virus Ankara promoter or active as a promoter in vaccinia virus infected cells.

3. The isolated DNA of claim 2, wherein no more than 5 nucleotides are substituted in the derivative relative to the sequence of SEQ ID NO:8, SEQ ID NO:9, SEQ ID NO:10, SEQ ID NO:11, or SEQ ID NO:12.

4. The isolated DNA of claim 2, wherein the isolated DNA consists of a derivative of SEQ ID NO:8, wherein no more than 10 nucleotides are substituted in the derivative relative to the sequence of SEQ ID NO:8.

5. The isolated DNA of claim 2, wherein the isolated DNA consists of a derivative of SEQ ID NO:9, wherein no more than 10 nucleotides are substituted in the derivative relative to the sequence of SEQ ID NO:9.

6. The isolated DNA of claim 2, wherein the isolated DNA consists of a derivative of SEQ ID NO:10, wherein no more than 10 nucleotides are substituted in the derivative relative to the sequence of SEQ ID NO:10.

7. The isolated DNA of claim 2, wherein the isolated DNA consists of a derivative of SEQ ID NO:11, wherein no more than 10 nucleotides are substituted in the derivative relative to the sequence of SEQ ID NO:11.

8. The isolated DNA of claim 2, wherein the isolated DNA consists of a derivative of SEQ ID NO:12, wherein no more than 10 nucleotides are substituted in the derivative relative to the sequence of SEQ ID NO:12.

9. The isolated DNA of claim 3, wherein the isolated DNA consists of a derivative of SEQ ID NO:8, wherein no more than 5 nucleotides are substituted in the derivative relative to the sequence of SEQ ID NO:8.

10. The isolated DNA of claim 3, wherein the isolated DNA consists of a derivative of SEQ ID NO:9, wherein no more than 5 nucleotides are substituted in the derivative relative to the sequence of SEQ ID NO:9.

11. The isolated DNA of claim 3, wherein the isolated DNA consists of a derivative of SEQ ID NO:10, wherein no more than 5 nucleotides are substituted in the derivative relative to the sequence of SEQ ID NO:10.

12. The isolated DNA of claim 3, wherein the isolated DNA consists of a derivative of SEQ ID NO:11, wherein no more than 5 nucleotides are substituted in the derivative relative to the sequence of SEQ ID NO:11.

13. The isolated DNA of claim 3, wherein the isolated DNA consists of a derivative of SEQ ID NO:12, wherein no more than 5 nucleotides are substituted in the derivative relative to the sequence of SEQ ID NO:12.

14. An expression cassette comprising:

a promoter comprising any one of the sequences of SEQ ID NO:3, SEQ ID NO:4, SEQ ID NO:6, SEQ ID NO:8, SEQ ID NO:9, SEQ ID NO:10, SEQ ID NO:11, and SEQ ID NO:12; and a coding sequence operably linked to the promoter;

wherein the expression of the coding sequence is controlled by the promoter; and wherein the expression cassette is not an expression cassette that naturally occurs in the genome of a vaccinia virus.

15. An expression cassette comprising:

a promoter comprising a derivative of any one of the sequences of SEQ ID NO:8, SEQ ID NO:9, SEQ ID NO:10, SEQ ID NO:11, and SEQ ID NO:12, wherein no more than 10 nucleotides are substituted in the derivative relative to the sequence of SEQ ID NO:8, SEQ ID NO:9, SEQ ID NO:10, SEQ ID NO:11, or SEQ ID NO:12, and a coding sequence operably linked to the promoter, wherein the expression of the coding sequence is controlled by the promoter, and wherein the expression cassette is not an expression cassette that naturally occurs in the genome of a vaccinia virus.

16. The expression cassette of claim 15, wherein no more than 5 nucleotides are substituted in the derivative relative to the sequence of SEQ ID NO:8, SEQ ID NO:9, SEQ ID NO:10, SEQ ID NO:11, or SEQ ID NO:12.

17. The expression cassette of claim 15, wherein the promoter comprises a derivative of SEQ ID NO:8, wherein no more than 10 nucleotides are substituted in the derivative relative to the sequence of SEQ ID NO:8.

18. The expression cassette of claim 15, wherein the promoter comprises a derivative of SEQ ID NO:9, wherein no more than 10 nucleotides are substituted in the derivative relative to the sequence of SEQ ID NO:9.

19. The expression cassette of claim 15, wherein the promoter comprises a derivative of SEQ ID NO:10, wherein no more than 10 nucleotides are substituted in the derivative relative to the sequence of SEQ ID NO:10.

20. The expression cassette of claim 15, wherein the promoter comprises a derivative of SEQ ID NO:11, wherein no more than 10 nucleotides are substituted in the derivative relative to the sequence of SEQ ID NO:11.

21. The expression cassette of claim 15, wherein the promoter comprises a derivative of SEQ ID NO:12, wherein no more than 10 nucleotides are substituted in the derivative relative to the sequence of SEQ ID NO:12.

22. The expression cassette of claim 14, wherein the coding sequence codes for therapeutic proteins or peptides, antigens, antigenic epitopes, antisense RNA, or ribozymes.

23. A vector comprising the expression cassette of claim 14.

24. The vector of claim 23, wherein the vector is a plasmid vector or a viral vector.

25. The vector of claim 24, wherein the vector is a vaccinia virus.

26. The vector of claim 25, wherein the vaccinia virus is Modified Vaccinia virus Ankara (MVA).

27. The vector of claim 26, wherein the vaccinia virus is strain MVA-BN deposited at the European Collection of Cell Cultures (ECACC) under number V00083008, strain MVA 572 deposited at ECACC under number V94012707, or strain MVA 575 deposited under number V00120707 at ECACC.

28. A host cell comprising the vector of claim 23.

29. A composition for inducing an immunological response in a living animal body comprising the viral vector of claim 24.

30. A method for introducing a coding sequence into a target cell comprising introducing the vector of claim 23 into the target cell.

31. A method for producing a peptide, protein, or virus comprising infection of a host cell with the viral vector of claim 24 and cultivating the infected host cell under suitable conditions.

32. The vector of claim 26, wherein the expression cassette is inserted into a naturally occurring deletion site of the MVA genome.

33. The vector of claim 26, wherein the expression cassette is inserted into an intergenic region of the MVA genome.

34. A composition comprising the vector of claim 23 with an adjuvant.

35. The expression cassette of claim 16, wherein the promoter comprises a derivative of SEQ ID NO:8, wherein no more than 5 nucleotides are substituted in the derivative relative to the sequence of SEQ ID NO:8.

36. The expression cassette of claim 16, wherein the promoter comprises a derivative of SEQ ID NO:9, wherein no more than 5 nucleotides are substituted in the derivative relative to the sequence of SEQ ID NO:9.

37. The expression cassette of claim 16, wherein the promoter comprises a derivative of SEQ ID NO:10, wherein no more than 5 nucleotides are substituted in the derivative relative to the sequence of SEQ ID NO:10.

38. The expression cassette of claim 16, wherein the promoter comprises a derivative of SEQ ID NO:11, wherein no more than 5 nucleotides are substituted in the derivative relative to the sequence of SEQ ID NO:11.

39. The expression cassette of claim 16, wherein the promoter comprises a derivative of SEQ ID NO:12, wherein no more than 5 nucleotides are substituted in the derivative relative to the sequence of SEQ ID NO:12.

40. The expression cassette of claim 16, wherein the coding sequence codes for therapeutic proteins or peptides, antigens, antigenic epitopes, antisense RNA, or ribozymes.

41. A vector comprising the expression cassette of claim 16.

42. The vector of claim 41, wherein the vector is a plasmid vector or a viral vector.

43. The vector of claim 42, wherein the vector is a vaccinia virus.

44. The vector of claim 43, wherein the vaccinia virus is Modified Vaccinia virus Ankara (MVA).

45. The vector of claim 44, wherein the vaccinia virus is strain MVA-BN deposited at the European Collection of Cell Cultures (ECACC) under number V00083008, strain MVA 572 deposited at ECACC under number V94012707, or strain MVA 575 deposited under number V00120707 at ECACC.

46. A host cell comprising the vector of claim 41.

47. A composition for inducing an immunological response in a living animal body comprising the viral vector of claim 42.

48. A method for introducing a coding sequence into a target cell comprising introducing the vector of claim 41 into the target cell.

49. A method for producing a peptide, protein, or virus comprising infection of a host cell with the viral vector of claim 42 and cultivating the infected host cell under suitable conditions.

50. The vector of claim 44, wherein the expression cassette is inserted into a naturally occurring deletion site of the MVA genome.

51. The vector of claim 44, wherein the expression cassette is inserted into an intergenic region of the MVA genome.

52. A composition comprising the vector of claim 41 with an adjuvant.

* * * * *